United States Patent
Jensen et al.

(10) Patent No.: US 6,409,993 B1
(45) Date of Patent: *Jun. 25, 2002

(54) DENTAL BLEACHING COMPOSITIONS INCORPORATING PERBORATES

(75) Inventors: Steven D. Jensen, South Jordan; Dan E. Fischer, Sandy, both of UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/433,442

(22) Filed: Nov. 4, 1999

(51) Int. Cl.$^7$ .............................. A61K 7/16; A61K 7/20
(52) U.S. Cl. .................. 424/53; 424/49; 433/215.1; 433/217.1
(58) Field of Search ...................... 424/49–58

(56) References Cited

U.S. PATENT DOCUMENTS

| | | | |
|---|---|---|---|
| 1,018,240 A | * 2/1912 | von Furegger | 424/53 |
| 2,501,145 A | * 3/1950 | Smith | 424/53 |
| 3,499,844 A | 3/1970 | Kibbel, Jr. et al. | 252/316 |
| 3,574,824 A | * 4/1971 | Echeand et al. | 424/53 |
| 3,657,413 A | 4/1972 | Rosenthal | 424/81 |
| 3,793,211 A | 2/1974 | Kohlhepp et al. | 252/99 |
| 3,936,385 A | 2/1976 | Cheng | 252/99 |
| 4,405,579 A | * 9/1983 | Smigez | 424/53 |
| 4,405,599 A | * 9/1983 | Smigez | 424/53 |
| 4,552,679 A | 11/1985 | Schobel et al. | 252/90 |
| 4,574,084 A | 3/1986 | Berger | 424/128 |
| 4,603,045 A | * 7/1986 | Smigez | 424/53 |
| 4,671,972 A | 6/1987 | Schobel et al. | 427/213 |
| 4,690,776 A | * 9/1987 | Smigez | 424/53 |
| 4,788,052 A | * 11/1988 | Ng et al. | 424/53 |
| 4,839,157 A | * 6/1989 | Ng et al. | 424/53 |
| 5,098,303 A | 3/1992 | Fischer | 433/215 |
| RE34,196 E | 3/1993 | Munro | 433/215 |
| 5,234,342 A | 8/1993 | Fischer | 433/215 |
| 5,240,415 A | * 8/1993 | Haynie | 424/53 |
| 5,256,402 A | 10/1993 | Prencipe et al. | 424/53 |
| 5,279,816 A | * 1/1994 | Church et al. | 424/53 |
| 5,648,064 A | * 7/1997 | Gaffar et al. | 424/53 |
| 5,785,527 A | 7/1998 | Jensen et al. | 433/215 |
| 5,855,870 A | 1/1999 | Fischer | 424/49 |
| 5,858,322 A | 1/1999 | Jensen et al. | 424/53 |
| 5,965,110 A | * 10/1999 | Arnold | 424/53 |
| 5,976,508 A | * 11/1999 | Nabi et al. | 424/53 |
| 5,985,249 A | 11/1999 | Fischer | 424/49 |
| 6,149,895 A | * 11/2000 | Kutsch | 424/53 |
| 6,274,122 B1 | * 8/2001 | McLauglin | 424/53 |
| 6,280,708 B1 | * 8/2001 | Ryles et al. | 424/53 |
| 6,309,625 B1 | * 10/2001 | Jensen et al. | 424/53 |
| 6,312,670 B1 | * 11/2001 | Montgomery | 424/53 |
| 6,312,671 B1 | * 11/2001 | Jensen et al. | 424/53 |
| 6,322,773 B1 | * 11/2001 | Montgomery | 424/53 |
| 6,322,774 B1 | * 11/2001 | Jensen et al. | 424/53 |

FOREIGN PATENT DOCUMENTS

| | | | |
|---|---|---|---|
| EP | 0 081 962 | 6/1983 | A61K/7/30 |
| EP | 0 451 105 A2 | 10/1991 | A61K/9/16 |
| FR | 404.344 | 12/1909 | |
| GB | 10589/40.552803 | 4/1943 | |
| WO | WO 96/25916 | 8/1996 | A61K/7/20 |

OTHER PUBLICATIONS

Dentistry Today Buyers' Guide to Whitening Systems Spp1 RGP Dental Inc VITINT System 19/V 0.5% Sodium Perborate/Glycerin Thick Gel 800–254–9695, Dec. 1997.*

* cited by examiner

*Primary Examiner*—Shep K. Rose
(74) *Attorney, Agent, or Firm*—Workman, Nydegger, Seeley

(57) ABSTRACT

Dental bleaching compositions that include perborate bleaching agents, such as sodium perborate monohydrate. The bleaching agent is dispersed within a sticky and viscous carrier such as a mixture of propylene glycol and silica fume. Anhydrous propylene glycol and/or anhydrous glycerin are especially useful in order to maintain the desired degree of hydration of the perborate being used. Flavorants may be added to enhance the taste of the dental compositions, since they will be used within a person's mouth. For best results, a flexible, thin-walled, comfortable-fitting, custom dental tray is used with the dental bleaching compositions. The dental compositions are sufficiently sticky and viscous so as to adhere and retain a dental tray against a person's teeth which is designed so as to not exert significant mechanical pressure onto the person's teeth.

24 Claims, No Drawings

DENTAL BLEACHING COMPOSITIONS INCORPORATING PERBORATES

BACKGROUND OF THE INVENTION

1. The Field of the Invention

The present invention relates to dental bleaching compositions and methods for bleaching teeth surfaces. More particularly, the present invention is directed to sticky and viscous dental bleaching compositions which incorporate a perborate bleaching agent, such as sodium perborate monohydrate. Such compositions are advantageously used in combination with a dental tray.

2. The Relevant Technology

Since its introduction in early 1989, there has been significant interest among the dental profession and the general public for home-use tooth bleaching products and methods. In its simplest form, home bleaching products typically include a dental bleaching composition having a form of hydrogen peroxide as the active bleaching agent. Some compositions are in the form of toothpastes that are simply brushed onto the teeth during a person's daily dental hygiene routine. Other, more specialized bleaching compositions are adapted for extended contact with the teeth to be bleached, such as by means of a dental tray.

As a general rule whitening toothpastes have largely been ineffective in whitening teeth due to their relatively low potency or concentration of active bleaching agent coupled with the short duration of contact of such formulations with a person's teeth. Because of the manner in which toothpastes are manufactured, shipped, stored and sold, toothpastes are largely incapable of incorporating higher concentrations of active bleaching agents that remain stable over the intended manufacturing and storage life of the toothpaste prior to use. Moreover, it is well-known that people typically brush for 60 seconds or less, thus further reducing the effectiveness of the already low concentration bleaching agent within over-the-counter toothpastes.

In view of the foregoing, bleaching compositions having increased bleaching activity coupled with methods that maintain such dental compositions in contact with the teeth for longer periods of time are necessary to effect a noticeable bleaching effect in most people. Typical dental bleaching compositions include from 5–20% by weight of carbamide peroxide ($CO(NH_2)_2 \cdot H_2O_2$), which is a complex of urea and hydrogen peroxide.

Such dental bleaching compositions are typically applied to a person's teeth using a dental tray configured so as to retain the dental composition against the person's teeth. A self-sealing dental "splint" that can be used with more fluid and less sticky dental bleaching compositions are disclosed in U.S. Pat. No. Re. 34,196 to Munro. Munro recommends the use of Proxigel®, manufactured according to U.S. Pat. No. 3,657,413 to Rosenthal, which at the time contained only 0.6% carboxypolymethylene as a thickening agent, or a mixture of Proxigel® and Peroxyl® gel, which is an even more fluid bleaching composition than Proxigel®. The Munro dental tray is especially suitable for use with such highly fluid dental compositions since it is made from a rigid plastic material and configured so as to form a fluid-tight seal against the person's gums. Such trays, however, are not always comfortable for the user, particularly when the dental tray is held in place over long periods of time within a person's mouth.

Flexible, more comfortable-fitting dental trays that are preferably used in combination with more sticky and viscous dental bleaching compositions are disclosed in U.S. Pat. Nos. 5,098,303 and 5,234,342, both to Fischer. Such dental trays, while being more flexible and generally thinner-walled compared to prior dental trays, are preferably trimmed in a preferred embodiment so as to terminate below the gingival margin and then scalloped up and around the interdental papilla. This provides maximum bleaching of the entire surface of the person's teeth while minimizing or eliminating actual contact with the person's gums, including the interdental papilla, thus providing minimum discomfort. Further enhancement of bleaching is provides by optionally building "reservoirs" into the dental trays so as to allow for increased loading of bleaching composition within the dental tray that can contact the teeth.

In some countries hydrogen peroxide and certain derivatives thereof such as carbamide peroxide are not permitted as dental bleaching agents. However, liquid or highly fluid perborate compositions have been allowed. Whereas the substitution of a perborate bleaching agent for hydrogen peroxide or carbamide peroxide may be desirable, simply substituting perborates for carbamide peroxide or hydrogen peroxide in a sticky and viscous bleaching composition is not straightforward. Many, if not most, peroxide-based dental bleaching compositions, such as those disclosed in U.S. Pat. No. 3,657,413 to Rosenthal and U.S. Pat. Nos. 5,098,303 and 5,234,342 to Fischer, use carboxypolymethylene as the primary or preferred thickening and tackifying agent. Unfortunately, the combination of sodium perborate monohydrate with carboxypolymethylene was found to be unstable. Under the conditions under which the inventors mixed carboxypolymethylene and sodium perborate monohydrate, a vigorous reaction ensued.

From the foregoing, it will be appreciated that what is needed in the art are improved compositions and methods for manufacturing suitable dental bleaching compositions that include perborates, such as sodium perborate.

Additionally, it would be a significant advancement in the art to provide dental bleaching compositions having a perborate as the active dental agent which also had sufficient stickiness and viscosity so as to enable such compositions to adhere and retain a comfortable-fitting dental tray in place for the duration of a desired treatment regimen.

It would be another significant advancement in the art to provide perborate-based dental bleaching compositions having the aforementioned level of stickiness and viscosity which were sufficiently stable so as to maintain the desired bleaching activity until bleaching of the teeth is desired.

Such dental bleaching compositions and methods for their manufacture and use are disclosed and claimed herein.

SUMMARY AND OBJECTS OF THE INVENTION

The present invention is directed to dental bleaching compositions used to treat tooth surfaces having a perborate bleaching agent. A preferred perborate bleaching agent is sodium perborate monohydrate, which has the formula $NaBO_3 \cdot H_2O$. The sodium perborate monohydrate is dispersed within a sticky carrier material, such as a mixture of an appropriate polyol and fumed silica. The sticky carrier material may include other gelling agents such as finely divided gel-forming metal oxides and/or organic thickeners known in the art and which are stable in the presence of sodium perborate monohydrate. Because the dental bleaching compositions according to the present invention are preferably sticky and viscous, they are especially suitable for use in combination with a custom dental tray that is designed so as to not exert significant mechanical pressure onto a person's teeth. The elimination or substantial reduction of mechanical pressures that are exerted onto a person's teeth during bleaching greatly increases the comfort experienced by the user. The inventive dental bleaching compositions are preferably formulated so as to a have a stickiness and viscosity that causes the bleaching compositions to adhere and retain a flexible, thin-walled dental tray against a person's teeth for as long as needed to carry out the desired bleaching process, such as the type of dental tray disclosed in U.S. Pat. Nos. 5,098,303 and 5,234,342, both to Fischer. For purposes of disclosing flexible, thin-walled, comfortable-fitting dental trays suitable for bleaching a person's teeth, the foregoing patents are incorporated herein by specific reference.

In order to carry out a desired bleaching process, the bleaching compositions of the present invention can be placed against a person's teeth for as little as 10 minutes and as long as 8 hours or more, depending on the potency of the bleaching composition and the desired level of bleaching. Preferably, the bleaching compositions will be placed over a person's teeth for at least about 30 minutes, more preferably for at least about 1 hour, and most preferably for at least about 2 hours. Depending on the desired treatment regimen, the dental bleaching compositions according to the present invention can vary in potency and stickiness in order to optimize the performance of the bleaching composition for a given treatment regimen.

An advantage of perborate-based bleaching agents rather than aqueous hydrogen peroxide or carbamide peroxide is that perborates are allowed for dental bleaching procedures in some countries that do not permit the use of aqueous hydrogen peroxide and carbamide peroxide for dental bleaching. Perhaps perborate compounds are more gentle on surrounding gums and tissues compared to either aqueous hydrogen peroxide or carbamide peroxide. Nevertheless, perborates were found to be unstable when blended with carboxypolymethylene, which is the tackifying agent of choice in the vast majority of home bleaching kits presently on the market. For this reason, a tackifying agent that is stable in the presence of perborate bleaching agents has been developed, which comprises a mixture of a suitable polyol and a finely divided gel-forming particulate such as fumed silica, otherwise known as silica fume.

It is, therefore, an object of the present invention to provide improved compositions and methods for manufacturing suitable dental bleaching compositions that include perborates, such as sodium perborate.

Another important object of the present invention is to provide dental bleaching compositions having a perborate as the active dental agent which also have sufficient stickiness and viscosity so as to enable such compositions to adhere and retain a suitable dental tray in place for the duration of a desired treatment regimen.

Yet another significant object of the present invention is to provide perborate-based dental bleaching compositions having the aforementioned level of stickiness and viscosity which are sufficiently stable so as to maintain the desired bleaching activity until bleaching of the teeth is desired.

These and other objects and features of the present invention will become more fully apparent from the description which follows, or may be learned by the practice of the invention.

DETAILED DESCRIPTION OF THE PREFERRED EMBODIMENTS

As summarized above, the present invention is generally related to dental bleaching compositions used to treat tooth surfaces having a perborate-based bleaching agent. The dental bleaching compositions are especially useful for use with flexible, thin-walled, comfortable fitting dental trays that are designed so as to not exert significant mechanical pressure onto a person's teeth.

The dental compositions manufactured according to the present invention include a perborate-based bleaching agent, typically an alkali metal perborate hydrate. A currently preferred perborate bleaching agent is sodium perborate monohydrate ($NaBO_3 \cdot H_2O$). Other known perborate bleaching agents include, but are not limited to, sodium perborate trihydrate, sodium tetrahydrate and perborates based on lithium and potassium. An advantage of using perborate-based bleaching agents rather than aqueous hydrogen peroxide or carbamide peroxide is that perborates have been allowed for use in bleaching teeth in countries that do not permit the use of aqueous hydrogen peroxide or carbamide peroxide for dental bleaching. In addition, perborates may be somewhat gentler on surrounding gingival tissues while still providing excellent tooth bleaching abilities.

In order to yield stable perborate-containing dental bleaching compositions, a sticky carrier material comprising finely divided silica, such as silica fume, dispersed in a liquid, such as a polyol, is used. In a preferred embodiment anhydrous propylene glycol and/or glycerin is employed in order to control the level of hydration of the perborate bleaching agent, which is currently sodium perborate monohydrate, during manufacture and storage. However, it is certainly within the scope of the invention to use non-anhydrous grades of propylene glycol or glycerin or even added water so long as the perborate bleaching agent remains stable within a desired range of stability. In addition to propylene glycol and glycerin, other polyols may be used as the liquid carrier, such as polypropylene glycols, sorbitol, polyethylene glycols, and the like.

Other gelling agents may be used in addition to fumed silica, such as finely divided alumina or other insoluble particulates that are capable of forming a gel when mixed with propylene glycol, glycerin and the like. In addition to finely divided inorganic particulate tackifying agents, organic tackifying agents known in the art can be added in order to adjust the viscosity and stickiness of the composition. Natural or synthetic polymers such as natural gums, proteins, cellulosic ethers, high molecular weight polyols, or other gel-forming admixtures, can be used. Examples of natural polymers include xanthan gum, gum arabic, gum tragacanth, gum karaya, starches, cellulosic ethers, proteins, and the like. The only limitation being that the thickening agent should be relatively stable when mixed with perborate bleaching agents in a desired concentration.

Even though the dental bleaching compositions of the present invention are based on perborate bleaching agents, it is certainly within the scope of the invention to add additional bleaching agents in order to enhance the capability of the dental bleaching compositions to bleach teeth. It may even be possible to include aqueous hydrogen peroxide, carbamide peroxide or other similar bleaching agents in addition to the perborate-based bleaching agent for use countries that permit such components for dental bleaching, or in order to yield compositions suitable for pharmaceutical or medical procedures.

Optional sweeteners and other flavorants can be added as desired to yield bleaching compositions having improved taste. A preferred sweetener is sodium saccharine, which has been found to be stable in the presence of perborate bleaching agents. In general any nutritive or non-nutritive sweeteners and other flavorants can be used so long as they yield a relatively stable bleaching composition that contains a perborate bleaching agent.

Colorants and other visual enhancing agents can be added as desired in order to yield a visually desirable dental bleaching composition. Other adjuvents and additives can also be added in minor amounts as needed to impart a desired property.

The dental bleaching agent is preferably included in an amount in a range from about 1% to about 50% by weight of the dental bleaching composition, more preferably in a range from about 10% to about 40% by weight, and most preferably in a range from about 20% to about 30% by weight of the dental bleaching composition. An example of a suitable perborate bleaching agent is sodium perborate monohydrate, which is available from Degussa, which is located in Germany.

The polyol is preferably included in an amount in a range from about 15% to about 90% by weight of the dental bleaching composition, more preferably in a range from about 30% to about 80% by weight, and most preferably in a range from about 45% to about 75% by weight of the dental bleaching composition. A presently preferred polyol is propylene glycol.

The fumed silica or similar finely divided particle capable of forming a sticky and viscous carrier when mixed with glycerin, including fumed silica or other finely divided particles blended with optional organic thickeners, is preferably included in an amount in a range from about 1% to about 40% by weight of the dental bleaching composition, more preferably in a range from about 5% to about 35% by weight, and most preferably in a range from about 10% to about 30% by weight of the dental bleaching composition. Fumed silica, precipitated silica and other appropriate finely divided particles that may be used to form a viscous and sticky carrier when mixed with one or more appropriate polyols will typically have a particle size from about 0.001 micron to about 1 micron. An example of a suitable silica fume that may be used to yield sticky and viscous dental bleaching compositions when mixed with a polyol is Aerosil 200, which is manufactured by Degussa. Although the dental bleaching compositions are not limited to the particular method or apparatus by which they are applied to a person's teeth, a preferred method for applying the dental bleaching compositions involves the use of a dental tray. A dental tray shields the composition from being rubbed off or diluted by saliva so that it can remain against the person's teeth during the desired treatment regimen. Virtually any dental tray known in the art could work in applying the inventive bleaching compositions disclosed herein.

In a preferred embodiment, flexible, comfortable-fitting, thin-walled dental trays that are designed so as to not exert significant mechanical pressure are used to apply the inventive dental bleaching compositions disclosed herein. The dental bleaching compositions are preferably sufficiently sticky and viscous so as to adhere and retain such dental trays in place for the duration of the desired treatment time. The dental trays may optionally be formed so as to include reservoirs in order to provide additional dental bleaching composition to one or more teeth of a dental arch needing more whitening than others, or to selected parts of a tooth needing more whitening than other parts. The dental trays are preferably trimmed to below the gingival margin and also scalloped up and around the interdental papilla. As stated above, preferred dental trays are manufactured according to U.S. Pat. Nos. 5,098,303 and 5,234,342 to Fischer, which have been previously incorporated by reference.

In order to carry out a desired bleaching process, the bleaching compositions of the present invention can be placed against a person's teeth for as little as 10 minutes and for as long as 8 hours or more, depending on the potency of the bleaching composition and the desired level of bleaching. Preferably, the bleaching compositions will be placed over a person's teeth for at least about 30 minutes, more preferably for at least about 1 hour, and most preferably for at least about 2 hours. Depending on the desired treatment regimen, the dental bleaching compositions according to the present invention can vary in potency and stickiness in order to optimize the performance of the bleaching composition for a given treatment regimen.

One currently preferred method of dispensing the bleaching agent uses a syringe. Squeezable tubes and other similar dispensing devices may also be used to dispense the bleaching agent. A syringe allows for the dispensing of a desired quantity of the dental bleaching composition, whether it be a unit dose or multiple doses. In the case of a syringe capable of providing for multiple doses of bleaching composition, graduations may be provided on the syringe to assist the user in dispensing a precise quantity of the bleaching composition each time.

The following examples set forth various exemplary dental bleaching compositions within the scope of the present invention. These examples are intended to be purely exemplary and should not be viewed as limiting the scope of the present invention.

EXAMPLE 1

A dental bleaching composition within the scope of the present invention was prepared by combining the following ingredients (in weight percent):

| | |
|---|---|
| Anhydrous Propylene Glycol | 54.3% |
| Fumed Silica | 20% |
| Sodium Perborate Monohydrate | 25% |
| Sodium Saccharine | 0.7% |

The fumed silica was Aerosil 200, which was obtained from Degussa in Germany, as was the sodium perborate monohydrate. The fumed silica was dispersed throughout the anhydrous propylene glycol in order to form a sticky and viscous carrier. Thereafter, the sodium perborate monohydrate and sodium saccharine were blended with the carrier in order to yield the dental bleaching composition.

The foregoing procedure produced a dental bleaching composition that was stable and which was able to adhere and retain a dental tray in place against a person's teeth. The dental bleaching composition was useful in bleaching the person's teeth.

EXAMPLE 2

A dental bleaching composition within the scope of the present invention was prepared by combining the following ingredients (in weight percent):

| | |
|---|---|
| Anhydrous Glycerin | 59.3% |
| Fumed Silica | 15% |
| Sodium Perborate Monohydrate | 25% |
| Sodium Saccharine | 0.7% |

The fumed silica was dispersed throughout the anhydrous glycerin in order to form a sticky and viscous carrier. Thereafter, the sodium perborate monohydrate and sodium saccharine were blended with the carrier in order to yield the dental bleaching composition.

The foregoing procedure produced a dental bleaching composition that was stable and which was able to adhere and retain a dental tray in place against a person's teeth. The dental bleaching composition was useful in bleaching the person's teeth.

EXAMPLE 3

A dental bleaching composition within the scope of the present invention is made according to the procedure of Example 1, except that the ingredients are combined in the following amounts (in weight percent):

| | |
|---|---|
| Anhydrous Glycerin | 75% |
| Fumed Silica | 20% |
| Sodium Perborate Monohydrate | 5% |

The resulting dental bleaching composition is sticky and viscous like the composition of Example 1 but has lower bleaching power.

EXAMPLE 4

A dental bleaching composition within the scope of the present invention is made according to the procedure of Example 1, except that the ingredients are combined in the following amounts (in weight percent):

| | |
|---|---|
| Anhydrous Glycerin | 77% |
| Fumed Silica | 22% |
| Sodium Perborate Monohydrate | 1% |

The resulting dental bleaching composition is sticky and viscous like the composition of Example 1 but has lower bleaching power.

EXAMPLE 5

A dental bleaching composition within the scope of the present invention is made according to the procedure of Example 1, except that the ingredients are combined in the following amounts (in weight percent):

| | |
|---|---|
| Glycerin | 50% |
| Fumed Silica | 12% |
| Sodium Perborate Monohydrate | 38% |

The resulting dental bleaching composition is sticky and viscous like the composition of Example 1 but has much higher bleaching power.

EXAMPLE 6

A dental bleaching composition within the scope of the present invention is made according to the procedure of Example 1, except that the ingredients are combined in the following amounts (in weight percent):

| | |
|---|---|
| Anhydrous Glycerin | 55% |
| Polyethylene glycol 300 | 10% |
| Fumed Silica | 15% |
| Sodium Perborate Monohydrate | 20% |

The resulting dental bleaching composition is sticky and viscous like the composition of Example 1 but has somewhat lower bleaching power.

EXAMPLE 7

A dental bleaching composition within the scope of the present invention is made according to the procedure of Example 1, except that the ingredients are combined in the following amounts (in weight percent):

| | |
|---|---|
| Propylene Glycol | 54.2% |
| Polyethylene glycol 300 | 5% |
| Water | 5% |
| Fumed Silica | 15% |
| Sodium Perborate Trihydrate | 20% |
| Sodium Saccharine | 0.8% |

The resulting dental bleaching composition is sticky and viscous like the composition of Example 1 but has somewhat lower bleaching power.

EXAMPLE 8

A dental bleaching composition within the scope of the present invention is made according to the procedure of Example 1, except that the ingredients are combined in the following amounts (in weight percent):

| | |
|---|---|
| Propylene Glycol | 59% |
| Xanthan Gum | 1% |
| Fumed Silica | 10% |
| Sodium Perborate Monohydrate | 30% |

The resulting dental bleaching composition is sticky and viscous like the composition of Example 1 but has somewhat higher bleaching power.

From the foregoing, it will be appreciated the present invention provides improved compositions and methods for manufacturing suitable dental bleaching compositions that include perborates, such as sodium perborate.

Additionally, it will be appreciated that the present invention further provides dental bleaching compositions having a perborate as the active dental agent which also have sufficient stickiness and viscosity so as to enable such compositions to adhere and retain a suitable dental tray in place for the duration of a desired treatment regimen.

It will be further appreciated that the present invention provides perborate-based dental bleaching compositions having the aforementioned level of stickiness and viscosity which are sufficiently stable so as to maintain the desired bleaching activity until bleaching of the teeth is desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A stable, one-part dental bleaching composition comprising:

at least one perborate dental bleaching agent included in an amount in a range from about 1% to about 50% by weight of the dental bleaching composition;

at least one liquid polyol; and a quantity of at least one finely divided particulate gelling agent which, when mixed with the liquid polyol, yields a sticky and viscous dental composition.

2. A dental bleaching composition as defined in claim 1, wherein the perborate dental bleaching agent comprises sodium perborate monohydrate.

3. A dental bleaching composition as defined in claim 1, wherein the perborate dental bleaching agent is included in an amount in a range from about 10% to about 40% by weight of the dental bleaching composition.

4. A dental bleaching composition as defined in claim 1, wherein the perborate dental bleaching agent is included in an amount in a range from about 20% to about 30% by weight of the dental bleaching composition.

5. A dental bleaching composition as defined in claim 1, wherein the liquid polyol comprises propylene glycol.

6. A dental bleaching composition as defined in claim 1, wherein the liquid polyol comprises anhydrous glycerin.

7. A dental bleaching composition as defined in claim 1, wherein the liquid polyol is included in an amount in a range from about 15% to about 90% by weight of the dental bleaching composition.

8. A dental bleaching composition as defined in claim 1, wherein the liquid polyol is included in an amount in a range from about 30% to about 80% by weight of the dental bleaching composition.

9. A dental bleaching composition as defined in claim 1, wherein the liquid polyol is included in an amount in a range from about 45% to about 75% by weight of the dental bleaching composition.

10. A dental bleaching composition as defined in claim 1, wherein the finely divided particulate comprises fumed silica.

11. A dental bleaching composition as defined in claim 1, wherein the finely divided particulate is included in an amount in a range from about 1% to about 40% by weight of the dental bleaching composition.

12. A dental bleaching composition as defined in claim 1, wherein the finely divided particulate is included in an amount in a range from about 5% to about 35% by weight of the dental bleaching composition.

13. A dental bleaching composition as defined in claim 1, wherein the finely divided particulate is included in an amount in a range from about 10% to about 30% by weight of the dental bleaching composition.

14. A dental bleaching composition as defined in claim 1, further including an organic polymer thickening agent.

15. A dental bleaching composition comprising:
at least one perborate dental bleaching agent included in an amount in a range from about 10% to about 50% by weight of the dental bleaching composition;
at least one liquid polyol included in an amount in a range from about 15% to about 90% by weight of the dental bleaching composition; and
at least one finely divided particulate gelling agent included in an amount in a range from about 5% to about 40% by weight of the dental bleaching composition and so as to yield a sticky and viscous dental bleaching composition.

16. A dental bleaching composition as defined in claim 15, further including an organic polymer thickening agent.

17. A dental bleaching composition as defined in claim 15, further including a flavorant.

18. A dental bleaching composition as defined in claim 1, wherein the dental bleaching composition has a stickiness and viscosity so that it is able to adhere and retain against a person's teeth a dental tray that is designed so as to not exert significant mechanical pressure onto the person's teeth and gums.

19. A dental bleaching composition as defined in claim 15, wherein the finely divided particulate gelling agent is included in an amount in a range of about 5% to about 35% by weight of the dental bleaching composition.

20. A dental bleaching composition as defined in claim 19, wherein the finely divided particulate gelling agent comprises fumed silica.

21. A substantially water free dental bleaching composition comprising:
at least one perborate dental bleaching agent included in an amount in a range from about 1% to about 50% by weight of the dental bleaching composition;
at least one liquid polyol that is substantially free of water, and
a quantity of at least one finely divided particulate gelling agent which, when mixed with the liquid polyol, yields a sticky and viscous dental composition that is substantially free of water.

22. A dental bleaching composition as defined in claim 21, wherein the finely divided particulate gelling agent comprises fumed silica.

23. A dental bleaching composition consisting essentially of:
at least one perborate dental bleaching agent included in an amount in a range from about 1% to about 50% by weight of the dental bleaching composition;
at least one liquid polyol; and
fumed silica included in an amount in a range of about 5% to about 40% by weight of the dental bleaching composition.

24. A dental bleaching composition as defined in claim 23, wherein the firmed silica is included in an amount in a range of about 5% to about 35% by weight of the dental bleaching composition.

* * * * *

UNITED STATES PATENT AND TRADEMARK OFFICE
CERTIFICATE OF CORRECTION

PATENT NO. : 6,409,993 B1
DATED : June 25, 2002
INVENTOR(S) : Steven D. Jensen and Dan E. Fischer It is certified that error appears in the above-identified patent and that said Letters Patent is hereby corrected as shown below:

Column 10,
Line 47, after "wherein the" change "firmed" to -- fumed --

Signed and Sealed this

Eleventh Day of February, 2003

JAMES E. ROGAN
*Director of the United States Patent and Trademark Office*